(12) United States Patent
Aubert et al.

(10) Patent No.: US 8,663,669 B2
(45) Date of Patent: Mar. 4, 2014

(54) PESTICIDE TREATMENT OF SOILS OR SUBSTRATES WITH SULPHUR COMPOUNDS

(75) Inventors: Thierry Aubert, Pau (FR); Jacques Auger, Veigne (FR)

(73) Assignee: Arkema France, Colombes Cedex (FR)

( * ) Notice: Subject to any disclaimer, the term of this patent is extended or adjusted under 35 U.S.C. 154(b) by 0 days.

(21) Appl. No.: 13/164,584

(22) Filed: Jun. 20, 2011

(65) Prior Publication Data

US 2012/0021032 A1 Jan. 26, 2012

Related U.S. Application Data

(63) Continuation of application No. 10/472,083, filed as application No. PCT/FR02/00768 on Mar. 4, 2002, now abandoned.

(51) Int. Cl.
*A01N 25/18* (2006.01)
(52) U.S. Cl.
USPC .............................. 424/405; 424/40; 514/707
(58) Field of Classification Search
None
See application file for complete search history.

(56) References Cited

U.S. PATENT DOCUMENTS

| 2,917,429 | A | 12/1959 | Webb et al. |
| 3,586,723 | A | 6/1971 | Alley |
| 5,013,350 | A | 5/1991 | Green et al. |
| 2003/0219355 | A1 | 11/2003 | Storkan et al. |

FOREIGN PATENT DOCUMENTS

| FR | 2779615 | 12/1999 |
| GB | 249830 | 8/1927 |
| JP | 5775906 | 5/1982 |
| JP | 01207204 | 8/1989 |
| JP | 11180807 | 7/1999 |

OTHER PUBLICATIONS

Database WPI, Section Ch, Week 199937, Class C03, AN, 1999-439334, XP002185561, Derwent Publications Ltd., London, GB.
Database Biosis 'Online!, Biosciences Information Service, May 1999, Bending Gary D et al., "Characterization of volatile sulphur-containing compounds produced during decomposition of *Brassica juncea* tissues in soil," Database Accession No. PREV199900258128, XP002185560, abstract, Philadelphia, PA, US; & Soil Biology & Biochemistry, vol. 31, No. 5, May 1999, pp. 695-703, ISSN: 0038-0717.
Patent Abstracts of Japan, Aug. 14, 1982, vol. 006, No. 154 (C-119).
Patent Abstracts of Japan, Nov. 17, 1989, vol. 013, No. 515 (C-655).
Database Biosis 'Online!, Biosciences Information Service, Entwistle A R et al., "Di allyl di sulfide to reduce the numbers Of sclerotia of *Sclerotium-cepivorum* in soil," Database Accession No. PREV198375013460, XP002185580, abstract, Philadelphia, PA; & Soil and Biology and Biochemistry, 1982, pp. 229-232, vol. 14, No. 3, ISSN: 0038-0717, cited in the application.
Auger J et al., "*Allium* spp thiosulfinates as substitute fumigants for Methyl Bromide," Pesticide Science, Feb. 1999, pp. 200-202, vol. 55, No. 2, XP000998147, ISSN: 0031-613X, cited in the application, Elsevier Applied Science Publisher, Barking, GB.
Masahiro Tada et al., "Nematicidal and antimicrobial constituents from *Allium grayi* Regel and *Allium fistulossum* L. var. caespitosum," Agric. Biol. Chem., 1988, pp. 2383-2385, vol. 52, No. 9, XP002185579, cited in the application, the whole document.
Auger et al., "Substances Sourfrees des *Allium* et des Cruciferes et Leurs Potentialites Phytosanitaires"; Biopesticides d'origine Vegetale, 2002, pp. 77-95.
Auger et al., Sulfur-containing Substances of the *Alliums* and the Crucifiers and their Crop-protection potential, 2002, 1-17.
Nammour et al.; "Insect Science and its Application"; The International Journal of Tropical Insect Science, vol. 10 (1), 1989, pp. 49-53.
Zettler et al., "Chemical Control of Stored Product Insects with Fumigants and Residual Treatments"; Crop Protection, vol. 19, 2000, pp. 577-582.
Wilson; "Four Years . . . and Counting"; World Grain; Feb. 2001, pp. 28-30.
Auger et al., "A Possible New Class of Natural Sulfur Pesticides for Fumigation"; Ecologie, vol. 25 (2), 1994, pp. 93-101.
Insects—The Yearbook of Agriculture—USDA, 1952 pp. 340-342.
Gooch; "The Contenders"; Pest Control, vol. 67 (1), p. 46, Jan. 1999.

*Primary Examiner* — Neil Levy
(74) *Attorney, Agent, or Firm* — Millen, White, Zelano & Branigan, P.C.

(57) ABSTRACT

In order to replace methyl bromide in all the uses thereof in soil or substrate treatment, the invention relates to the use of at least one sulphur compound having general formula: wherein R represents an alkenyl or alkyl radical, n is equal to 0, 1 or 2, x is a number between 0 and 4 and R' represents an alkenyl or alkyl radical or, only if n=x=0, a hydrogen or alkali-metal atom. The sulphur compounds (in particular dimethyldisulphide) can be applied according to standard soil treatment methods (by injection, spraying, dripping, sprinkling) and said compounds have no phototoxic effects.

4 Claims, No Drawings

PESTICIDE TREATMENT OF SOILS OR SUBSTRATES WITH SULPHUR COMPOUNDS

This application is a continuation of U.S. patent application Ser. No. 10/472,083, filed Sep. 17, 2003 now abandoned, which is incorporated by reference herein.

The invention relates to the field of agriculture and more particularly its subject is the replacement of methyl bromide in all its uses for treating soils or plant substrates (compost, peat, rock wool and the like), in particular those intended for agriculture for controlling therein nematodes, pathogenic fungi, insect pests and bacteria.

Currently, the disinfection of soils or substrates, for example those intended for intensive agriculture and in particular those intended for aboriculture, horticulture and market gardening, is predominantly carried out by fumigation with methyl bromide (world consumption greater than 70 000 tons), this compound exhibiting in the gaseous state excellent, nematicidal, fungicidal, insecticidal and bactericidal properties. Unfortunately, this compound contributes to depletion of the ozone layer and, in accordance with the Montreal accord (1992), by 2005 it should no longer be used in industrialized countries. There is therefore an urgent need to provide users with substitutes which are equally effective and which are as environmentally friendly as possible. In spite of the continuous efforts made both by governmental organizations and private bodies, no substitute has yet been found which is capable, on its own and at the same cost, of replacing methyl bromide in all its uses with the same efficacy (cf. USDA Report, Vol. 6, No. 4 and Citrus & Vegetable Magazine, Methyl Bromide Update: Spring 2000). Indeed, the main substitutes currently proposed are highly toxic and therefore require respiratory protection which is expensive and not very convenient (case of dichloropropene) or their application is delicate and they therefore give variable results (case of Metam-sodium and tetrathio-carbonate) or they are considerably more expensive (case of methyl iodide).

To our knowledge, the only sulphur compounds envisaged as substitutes for methyl bromide are methyl isothiocyanate (MITC), tetrathiocarbonate or MITC-generating compounds such as Metam-sodium and Dazomet.

Despite the considerable efforts made by the scientific community since the banning of methyl bromide, few molecules have been found which are capable of replacing it in its application in the fumigation of soils or of substrates although there are hundreds of pesticides available (more than 700 nematicides, fungicides, insecticides, bactericides recorded in the Pesticide Manual, Tenth edition, Ed. Clive Tombin). The reason is the need for fumigants to meet two essential conditions: on the one hand, they should not exhibit, at the doses at which they are active, any phytotoxicity on the crops put in place after the treatment and, on the other hand, they should have the essential and rare property of not being completely absorbed into soils and of diffusing rapidly, in gaseous form, in the thickness of the soil to be treated, the pathogenic organisms being often present up to at least 50 cm below the surface of the soil; furthermore, for obvious reasons of productivity, and in order to limit the risk of reinfestation, the treatment time during which the fumigant acts should be as short as possible.

A few scattered items of information exist in the literature on the specific activity of certain sulphur-containing substances with respect to various pathogenic organisms: that is the case for example for disulphides which prevent the larvae of nematodes from leaving the cysts (patent GB 249 830) or which act on insects of the coleoptera or lepidoptera type which are present in stored foodstuffs (Pestic. Sci. Vol. 55, 1999, pages 200-202); diallyl disulphides have a fungicidal action on the sclerotia of S. cepivorum (Soil Biology and Biochemistry, Vol. 14, No. 3, pages 229-232); the nematicidal properties of disulphides or trisulphides derived from certain alliums on nematodes of the Meloidogyne incognita type are described in the article Agric. Biol. Chem. 52 (9) 1988, pages 2383-2385. The thiosulphinates (n=x=1) are described in the literature as nematicides (JP 01 207 204), as fungicides and antibacterials (JP 57 075 906), as nematicides and antimicrobials (Agric. Biol. Chem., 1988, 52(9), pages 2383-2385), as insecticides against the insects of stored foodstuffs (Pestic. Sci. Vol. 55, 1999, pages 200-202). The insecticidal activity of the vapours derived from ground products of allium containing, inter alia, disulphides and thiosulphinates has been demonstrated in Patent Application FR-A-2 779 615 proposing the use of these ground products for the fumigation treatment of stored foodstuffs. However, for persons skilled in the art, it is a priori not obvious that a fumigant for stored foodstuffs may be suitable for application in the treatment of soils or substrates. Indeed, as explained in column 3 (lines 8-54) of U.S. Pat. No. 5,518,692 recommending methyl iodide as a substitute for methyl bromide, soil is a much more complex medium than stored foodstuffs (nonuniform moisture, particles of widely varying diameters, and the like) and the organisms to be controlled are a lot more numerous and varied in the case of soils. Consequently, most fumigants used for stored foodstuffs are not used for the fumigation of soils.

There is no information in the prior art on a global pesticidal activity of these substances, that is to say a simultaneous nematicidal, fungicidal, insecticidal and bactericidal activity. The nematicidal, fungicidal and bactericidal activity of dimethyl polysulphides (having a number of sulphur atoms greater than or equal to 3) is described in U.S. Pat. No. 2,917,429 but no mention is made of the insecticidal properties and dimethyl disulphide is reported as having a zero activity on a large number of fungi.

It has now been found that the sulphur compounds of general formula:

$$R-\underset{\underset{(O)_n}{\|}}{S}-S_x-R' \qquad (I)$$

in which R represents an alkyl or alkenyl radical containing from 1 to 4 carbon atoms, n is equal to 0, 1 or 2, x is a number ranging from 0 to 4, and R' represents an alkyl or alkenyl radical containing from 1 to 4 carbon atoms or, only if n=x=0, a hydrogen or alkali metal atom, are particularly advantageous for the fumigation of soils and substrates because they fulfil three essential conditions in order to be able to be used practically for disinfecting soils or substrates: they exhibit global pesticidal (nematicidal, fungicidal, insecticidal and bactericidal) properties: they are capable of rapidly diffusing in the thickness of the soil to be treated, giving a sufficient gas concentration to kill the pathogenic organisms present; at the doses necessary for killing these pathogenic organisms, the compounds of formula (I) exhibit no phytotoxicity on the crops put in place after the treatment. This set of essential properties for the application envisaged has never been previously described for the compounds of formula (I).

As substitutes for methyl bromide, the compounds of formula (I) are all the more advantageous since some of them are already present in nature, being derived from the natural degradation of crucifers and alliums. In particular, the thiosulphinates, included in general formula (I), are products which are naturally emitted when alliums are ground and, as such, they can be used in biological agriculture. Moreover, given that they do not contain halogen atoms which generate halogenated radicals responsible for the catalytic destruction of the stratospheric ozone, the compounds of formula (I) are without danger for the ozone layer.

As nonlimiting examples of radicals R and R', there may be mentioned the methyl, propyl, allyl and 1-propenyl radicals. Among the compounds of formula (I), the compounds for which n=0 are preferred. Other preferred compounds are the disulphides (n=0, x=1) and more particularly dimethyl disulphide (DMDS).

The compounds of formula (I) may be used in the pure state or in various forms which, depending on the nature of the compound (I), may be an aqueous emulsion, a microemulsion, a product which is microencapsulated or supported by a solid, a solution in water, in an organic solvent or as a mixture with a product which can itself have an activity for the treatment of soils.

All these formulations may be prepared according to methods well known to persons skilled in the art. Thus, for example, the aqueous emulsions and the microemulsions may be obtained by adding one or more surfactants to the compound of formula (I), and then in adding to the mixture obtained a certain quantity of water so as to obtain a stable emulsion or a microemulsion.

Surfactants which are rather hydrophilic, that is to say those having an HLB ("Hydrophilic Lipophilic Balance") greater than or equal to 8, which may be of anionic, cationic, nonionic or amphoteric nature, are more particularly suitable for the preparation of the aqueous emulsions or microemulsions. As nonlimiting examples of anionic surfactants, there may be mentioned:

alkali or alkaline-earth metal, ammonium or triethanolamine salts of alkyl-, aryl- or alkylaryl-sulphonic acids, fatty acids with a basic pH, sulphosuccinic acid or alkyl, dialkyl, alkylaryl or polyoxyethylenealkylaryl esters of sulphosuccinic acid, alkali or alkaline-earth metal salts of esters of sulphuric, phosphoric, phosphonic or sulphoacetic acid and saturated or unsaturated fatty alcohols, and their alkoxylated derivatives, alkali or alkaline-earth metal salts of alkylaryl-sulphuric, alkylarylphosphoric or alkylarylsulphoacetic acids, and their alkoxylated derivatives.

The cationic surfactants which may be used are, for example, those of the family of quaternary alkylammoniums, sulphoniums or fatty amines with acidic pH, and their alkoxylated derivatives.

As nonlimiting examples of nonionic surfactants, there may be mentioned ethoxylated alkylphenols, ethoxylated alcohols, ethoxylated fatty acids, fatty esters of glycerol or fatty derivatives of sugar.

The amphoteric surfactants which may be used are, for example, alkylbetaines or alkyltaurines.

The preferred surfactants for the preparation of the aqueous emulsions and microemulsions are compounds based on alkyl benzenesulphonate and alkoxylated alkylphenol.

The organic solvents which may be used to dissolve the compounds of formula (I) according to the invention are hydrocarbons, alcohols, ethers, ketones, esters, halogenated solvents, mineral oils, natural oils and their derivatives, and aprotic polar solvents such as dimethylformamide, dimethyl sulphoxide or N-methylpyrrolidone. Biodegradable solvents, more particularly methyl esters of rapeseed oils, are particularly suitable.

The products with pesticidal activity which are particularly suitable for mixing with the compounds of formula (I) according to the invention are pure products such as 1,3-dichloropropene or chloropicrin ($Cl_3C-NO_2$) which are themselves used as fumigants, aqueous solutions of products such as Metam-sodium ($CH_3-NH-CS_2^-Na^+$) or sodium tetrathiocarbonate ($Na_2CS_4$) which are also used as fumigants, or any other product having an activity which is complementary to or synergistic with the compounds of formula (I), such as MITC ($CH_3-NCS$) or Dazomet (generator of MITC).

The compounds of formula (I) and the compositions containing them may be applied according to any of the conventional methods for introducing pesticides into the soil, such as, for example, injection by coulters which makes it possible to introduce the product deep, spraying on the soil, drip by a conventional irrigation system or "sprinkler" type sprinkling. After introducing the product into the soil and optionally spreading (for example using a rotary spade in the case of injection into the soil), the surface of the soil may be optionally closed, either by capping the surface by means of a smoothing roller, or with a plastic film.

The doses of compound (I) to be used in order to obtain the desired effect are generally between 150 and 1 000 kg/ha and depend on the nature of the compound (I), the level of soil infestation, the nature of the pests and of the pathogenic organisms, the type of crop and soil, and the application methods. At these doses, the desired general pesticidal (nematicidal, fungicidal, insecticidal and bactericidal) effect and no phytotoxic effect is observed.

There will be no departure from the scope of the present invention by combining the treatment with a compound of formula (I) with a treatment (simultaneous or otherwise) with one or more other pesticidal substances.

The following examples illustrate the invention without limiting it.

EXAMPLE 1

Formulations

EXAMPLE 1a

Aqueous emulsions having sufficient stability to allow homogeneous application of the product to the soil after the preparation of the emulsion can be obtained by mixing:

692 g of dimethyl disulphide, 38.5 g of Toximul® D, 38.5 g of Toximul® H (2 surfactants marketed by the company Stepan, based on alkyl benzenesulphonate and alkoxylated alkylphenol in alcoholic solution), and 9 230 g of water: formulation A.

1 800 g of dimethyl disulphide, 160 g of Toximul® DH68, 40 g of Toximul® DM83 (2 surfactants marketed by the company Stepan, based on alkyl benzenesulphonate), and 8 000 g of water: formulation B.

1 600 g of dimethyl disulphide, 320 g of Toximul® DH68, 80 g of Toximul® DM83 (2 surfactants marketed by the company Stepan, based on alkyl benzenesulphonate), and 8 000 g of water: formulation C.

EXAMPLE 1b

A water-dimethyl disulphide microemulsion may be prepared by adding 4 400 g of water to a mixture of 4 400 g of dimethyl disulphide, 960 g of Toximul® DH68 and 240 g of Toximul® DM83 (2 surfactants marketed by the company Stepan, based on alkyl benzenesulphonate): formulation D.

EXAMPLE 1c

A solution of dimethyl disulphide in rapeseed methyl ester, a biodegradable solvent which makes it possible to increase the flash point of the preparation to be applied and therefore to improve the safety of the applicator, may be obtained by dissolving 3 000 g of dimethyl disulphide in 7 000 g of rapeseed methyl ester: formulation E.

EXAMPLE 2

Phytotoxicity

EXAMPLE 2a

The absence of phytotoxicity of dimethyl disulphide (DMDS) applied in the form of formulation A, in the dose range where it is effective on pathogenic soil organisms, was demonstrated on young cucumber plants (9 cm, 2 leaves, ARIS hybrid) and young tomato plants (13 cm, 3 leaves, JUMBO hybrid):

For both types of crop, 4 treatments were performed on 20 plants:
  untreated control
  360 kg/ha of DMDS
  540 kg/ha of DMDS
  720 kg/ha of DMDS Five days after the treatment, the young plants are transplanted into pots 20 cm in diameter and 35 cm in height.

The observations relating to the number of leaves per plant and the visual state of the plants are carried out 15 and 41 days after the transplantation:

TABLE 1

Average number of leaves per plant

| Treatment | Tomato after 15 days | Tomato after 41 days | Cucumber after 15 days | Cucumber after 41 days |
|---|---|---|---|---|
| Untreated control | 5.5 | 9.7 | 5.4 | 9.8 |
| DMDS: 360 kg/ha | 5.3 | 9.6 | 5.3 | 9.8 |
| DMDS: 540 kg/ha | 5.3 | 9.4 | 5.7 | 9.7 |
| DMDS: 720 kg/ha | 5.7 | 9.8 | 5.7 | 9.9 |

The results of Table 1 show that there is no significant difference between the untreated control and the plants treated with DMDS, regardless of the concentration tested; furthermore, no visual symptom of phytotoxicity was detected.

EXAMPLE 2b

Absence of phytotoxicity on lettuce of DMDS, applied at 150 kg/ha, in the open, in a greenhouse.
1. Materials and methods
Lettuce variety: Sprintia
Treatment: DMDS is applied in the form of formulation A with the aid of a jet sprayer, and then incorporated over a depth of about 5 cm with a rotary hoe. The soil is then covered with a black polyethylene film.
Planting: 7 days after the treatment, at the rate of 160 000 plants/ha
Harvesting: 2 months and 20 days after planting.
2. Results Visual observations on the field 1 and 2 months after planting revealed no sign of phytotoxicity. At harvest, the average weight of the lettuce treated with DMDS was measured and found to be equal to 505 g, compared with 490 g for the control with no treatment. It can therefore be concluded that the treatment carried out with DMDS is without phytotoxic effect on lettuce.

EXAMPLE 3

Diffusion into the Soil

The rate of diffusion of DMDS was studied by filling a sealed thermal glass chamber of 3.3 litres and 40 cm in height with 2.5 litres of earth (that is 33 cm) obtained from the Garonne valley (sandy-muddy soil containing 1.6% of organic matter); the DMDS was deposited at the surface of the earth in 2 doses: 300 and 800 kg/ha, that is, considering a disinfection over 30 cm, doses of 100 and 266.6 $g/m^3$ of soil. There are then measured by gas chromatography, as a function of time (in hours), the concentrations of DMDS in gaseous form (in $g/m^3$) in the top free volume of the chamber (point A) and at 11 cm (point B), 22 cm (point C) and 33 cm (point D) below the level of the earth by means of 3 openings equipped with sealed septums on the side of the chamber; the variation in the concentration as a function of time for the 4 measurement points is thus obtained, as shown in Table 2 in the case of the 800 kg/ha dose.

TABLE 2

DMDS concentrations in $g/m^3$ - case of the 800 kg/ha dose

| Time in h | A (0 cm) | B (−11 cm) | C (−22 cm) | D (−33 cm) |
|---|---|---|---|---|
| 0 | 0 | 0 | 0 | 0 |
| 1 | 144.9 | 76.6 | 3 | 0 |
| 3 | 152.7 | 73.9 | 5.1 | 0.3 |
| 5 | 96.3 | 63.8 | 48.4 | 21.5 |
| 5.5 | 123.7 | 91.4 | 58.3 | 29.4 |
| 24 | 32.7 | 30.2 | 40.1 | 34.4 |
| 96 | 11.8 | 11.5 | 12.9 | 14.6 |

Table 2 shows that approximately 24 hours are sufficient for the DMDS concentration to be homogeneous in the entire thickness of the column of earth.

The product CT of the concentrations C by the time of measurement T is another essential data which indicates the cumulative doses of DMDS to which are subjected the pathogenic organisms which may be present at the different measurement points. The CT values in $gh/m^3$ indicated in Table 3 are thus found for the two concentrations tested.

TABLE 3

| Doses | A (0 cm) | B (−11 cm) | C (−22 cm) | D (−33 cm) |
|---|---|---|---|---|
| 300 kg/ha | 3187 | 2737 | 2753 | 2210 |
| 800 kg/ha | 4145 | 3327 | 3276 | 2809 |

The CT values measured are therefore of the order of 2 500 $gh/m^3$ for a dose of 300 kg/ha and 3 000 $gh/m^3$ for a dose of 800 kg/ha.

EXAMPLE 4

Fungicidal Properties

The fungicidal effect of DMDS was demonstrated on four of the common pathogenic organisms which are damaging to the principal market garden crops described in the article "Désinfecter les sols autrement" [Disinfecting soils differently] published in June 1999 in the CTIFL (Centre technique interprofessionnel des fruits et légumes) review. These four organisms are the following:

*Phytophthora cactorum*, one of the best known representatives of the *Phytophthora* family, polyphagous fungi which attack mainly tomato, sweet pepper and strawberry plants, these three crops representing the majority of the worldwide consumption of methyl bromide. *Phytophthora cactorum*, in particular, attacks mainly the strawberry plant and fruit trees.

*Rhizoctonia solani*: a very important group of polyphagous pathogens in the genus *Rhizoctonia* and which attack very many market garden crops including sweet pepper and lettuce.

*Sclerotinia sclerotiorum*: polyphagous fungus which attacks mainly melon crops.

*Sclerotium rolfsii*: a fungus which is also polyphagous and which is found, for example, on melon and courgette crops.

These four fungi were studied in the following form:
*Sclerotinia sclerotiorum*: sclerotia
*Sclerotium rolfsii*: sclerotia
*Rhizoctonia solani*: colonized barley grains (mycelium and sclerotia)
*Phytophthora cactorum*: colonized millet grains (mycelium, sporangia and oospores)

Preparation of the Fungi (24 h Before the Gassing Operation)
1. Preparation of the sclerotia of *Sclerotinia sclerotiorum* and of *Sclerotium rolfsii*: The fungi are cultured on malt agar medium until the sclerotia are obtained. The sclerotia are collected in a sterile manner and stored dry in empty Petri dishes until they are used. The sclerotia used for the trial are over 3 months old and are perfectly dormant.
2. Preparation of *Phytophthora cactorum* and of *Rhizoctonia solani*:
The millet and barley used for the multiplication of the two fungi are moistened with ultrapure water by immersing for 24 hours. The grains are then slightly drained and then distributed into flasks and autoclaved (3 autoclavings at 110° C. for 20 minutes, 3 times at 24 hour intervals). Fragments of fungal culture are introduced into the flasks which are then incubated at 22° C.±2° C. (white light 18 h) until homogeneous colonization is obtained. The grains are then removed from the flasks in a sterile manner, dried in the sterile stream of a safety cabinet and then stored in the dry state until they are used.

Conditions for Gassing and for Desorption

All the batches of fungi to be treated are placed for a few hours at the trial temperature (20° C.). Between 35 and 300 units of fungi or "propagules" (grains or sclerotia) are subjected to gassing during each trial.

Each fumigation chamber comprising to one or more species of fungi corresponds to a glass round-bottomed flask which is impervious to the gas and has a volume of 1 l litres. Each round-bottomed flask is equipped with branch connections, one at the bottom for introducing the liquid DMDS, one at the top for collecting the air sample with a syringe.

Before introducing the gas, a partial vacuum (−500 mbar) is established in the round-bottomed flask with a vacuum pump. This makes it possible, on the one hand, to avoid the phenomenon of excess pressure due to the expansibility of DMDS in the round-bottomed flask and, on the other hand, to promote better homogeneity of the air-gas mixture in the first few seconds which follow injection. The DMDS (weighed accurately to the mg) is injected with a syringe, in liquid form, through the bottom branch connection, that is to say under the screen placed at half height of the round-bottomed flask and supporting the batches of fungi. After introducing the product, the internal pressure of the round-bottomed flask is re-established at atmospheric pressure. A magnetic stirrer operates during the entire duration of the treatment in order to properly homogenize the air-gas mixture.

At the end of the gassing, the cover for the round-bottomed flask is removed. One minute after this operation, the batches of fungi gassed are taken out and left in the open air for 15 minutes for desorption of the DMDS. They are then transferred into a Petri dish, the latter remaining open for 5 minutes to allow perfect desorption of the gas.

Measurement of the Gas Concentrations

The mean concentration (C in g/m$^3$) of DMDS in the fumigation chamber after homogenization of the gas in the chamber air is measured by GC with an FID detector and, taking into account the duration of exposure (T in hours), the product CT (g·h/m$^3$) is calculated which, in the field of fumigation, is the key parameter to be considered, since the biological efficacy of a gas towards a given pathogenic agent is only effective if the latter was exposed to a certain mean concentration C for a certain duration of exposure T, that is to say to a certain value of the product CT, a value (or dose) which can be reached in different ways: low concentrations and long duration of exposure or conversely.

Conditions for Reading the Results

Grains: After gassing, the grains are deposited on a selective medium in an amount of 5 to 10 per Petri dish of 90 mm (*Rhizoctonia*: Malt agar; *Phytophthora*: Malt agar+Pimaricin, Ampicillin, Rifampicin, Benomyl).

Sclerotia: After gassing, the sclerotia are superficially disinfected with Javel water (1% NaOCl), rinsed twice with sterile water, and then deposited in an amount of one per dish on a malt agar-chloramphenicol medium (200 ppm).

Expression of the Results

The number of propagules giving rise to a colony (viable propagules) are noted daily until there are no changes, and at most 19 days after the day of gassing.

The results are expressed as:
viability (V), that is to say the percentage of viable propagules giving rise to a colony
reduction in viability (Rv) compared with the control, that is to say:

$$R_v = \frac{V_{control} - V}{V_{control}} \times 100$$

vitality score (Nm): to each propagule which has given rise to a colony, a score (N) is attributed which describes how fast this propagule develops; this score, equal to the difference between the total number of days of observation (19 maximum) and the number of days between depositing in a Petri dish and the development of the colony, is higher, the closer the appearance of the colony to the date of depositing in a Petri dish. For each of the trials, a mean (Nm) of the scores attributed is then calculated.

reduction in vitality score ($R_{Nm}$) compared with the control, that is to say:

$$R_{Nm} = 100 - \frac{Nm}{Nm_{control}} \times 100$$

Results
1. Biological Efficacy of DMDS on *Phytophthora cactorum*

The results assembled in Table 4 clearly show that, at CT doses greater than 2 500 g·h/m$^3$ approximately, the fungicidal efficacy progresses regularly with the CT dose: reduction in viability and vitality score. Total efficacy (0% viability) is obtained at about 3 500 g·h/m³.

TABLE 4

Summary of all the readings expressed in terms of viability and vitality on *Phytophthora cactorum* (X = number of grains)

| | | | | Viability | | Vitality | |
| | | | | | | Nm (over | |
| X | C | T | CT | V | RV | 12 days) | RNm |
|---|---|---|---|---|---|---|---|
| 60 | 17.46 | 24 | 419 | 91.7 | 6.8 | 7.7 | 15.5 |
| 60 | 26.04 | 24 | 625 | 100 | −1.7 | 8.05 | 11.9 |
| 60 | 29.29 | 24 | 703 | 100 | −1.7 | 8.3 | 9.1 |
| 60 | 37.79 | 24 | 907 | 100 | −1.7 | 7.2 | 21.2 |
| 60 | 15.91 | 66 | 1 050 | 95 | 5.0 | 5.5 | 43.1 |
| 90 | 21.24 | 66 | 1 402 | 97.8 | 2.2 | 6.6 | 32.2 |
| 60 | 30.96 | 48 | 1 450 | 95 | 3.4 | 5.4 | 40.7 |
| 90 | 28.77 | 66 | 1 899 | 97.8 | 2.2 | 5.6 | 42.6 |
| 90 | 30.02 | 66 | 1 981 | 97.8 | 2.2 | 5.3 | 45.7 |
| 60 | 51.25 | 48 | 2 460 | 43.3 | 55.9 | 1.7 | 81.2 |
| 300 | 37.44 | 66 | 2 471 | nm* | nm* | nm* | nm* |
| 90 | 42.98 | 66 | 2 837 | 16.7 | 83.3 | 0.6 | 93.6 |
| 300 | 45.06 | 66 | 2 974 | nm* | nm* | nm* | nm* |
| 90 | 48.02 | 66 | 3 169 | 1.1 | 98.9 | 0.05 | 99.5 |
| 300 | 52.53 | 66 | 3 467 | 0 | 100 | 0 | 100 |

*nm = not measured

2. Biological Efficacy of DMDS on *Rhizoctonia solani*

The results assembled in Table 5 clearly show that at CT doses greater than 2 000 g·h/m³ approximately, the fungicidal efficacy progresses regularly with the CT dose: reduction in viability and vitality score. Total efficacy (0% viability) is obtained at about 3 500 g·h/m³.

TABLE 5

Summary of all the readings expressed in terms of viability and vitality on *Rhizoctonia solani* (X = number of grains)

| | | | | Viability | | Vitality | |
| | | | | | | Nm (over | |
| X | C | T | CT | V | RV | 11 days) | RNm |
|---|---|---|---|---|---|---|---|
| 60 | 17.46 | 24 | 419 | 100 | 0 | 9.0 | 0 |
| 60 | 26.04 | 24 | 625 | 100 | 0 | 8.7 | 3.1 |
| 70 | 29.29 | 24 | 703 | 100 | 0 | 8.3 | 7.3 |
| 70 | 37.79 | 24 | 907 | 100 | 0 | 7.1 | 21.6 |
| 65 | 15.91 | 66 | 1 050 | 89.2 | 10.8 | 7.0 | 22.2 |
| 65 | 21.24 | 66 | 1 402 | 96.9 | 3.1 | 7.6 | 15.0 |
| 65 | 30.96 | 48 | 1 450 | 98.5 | 1.5 | 4.4 | 51.3 |
| 70 | 28.77 | 66 | 1 899 | 84.3 | 15.7 | 6.0 | 33.2 |
| 75 | 30.02 | 66 | 1 981 | 94.7 | 5.3 | 7.4 | 17.2 |
| 73 | 51.25 | 48 | 2 460 | 11.0 | 89.0 | 0.3 | 96.2 |
| 286 | 37.44 | 66 | 2 471 | 24.1 | 75.9 | 0.6 | 92.0 |
| 90 | 42.98 | 66 | 2 837 | 2.2 | 97.8 | 0.1 | 98.4 |
| 286 | 45.06 | 66 | 2 974 | 9.4 | 90.6 | 0.1 | 98.4 |
| 80 | 48.02 | 66 | 3 169 | 1.2 | 98.8 | 0.05 | 99.3 |
| 290 | 52.53 | 66 | 3 467 | 0 | 100 | 0 | 100 |

3. Biological Efficacy of DMDS on *Sclerotinia sclerotiorum*

The results assembled in Table 6 clearly show that at CT doses greater than 1 000 g·h/m³ approximately, the fungicidal efficacy progresses regularly with the CT dose: reduction in viability and vitality score. Total efficacy (0% viability) is obtained at about 3 500 g·h/m³, considering that the point CT 3467 is an abnormal point.

TABLE 6

Summary of all the readings expressed in terms of viability and vitality on *Sclerotinia sclerotiorum* (X = number of grains)

| | | | | Viability | | Vitality | |
| | | | | | | Nm (over | |
| X | C | T | CT | V | RV | 19 days) | RNm |
|---|---|---|---|---|---|---|---|
| 39 | 17.46 | 24 | 419 | 89.7 | −3.0 | 13.3 | −3.6 |
| 41 | 26.04 | 24 | 625 | 87.8 | −0.8 | 12.8 | 0.1 |
| 41 | 29.29 | 24 | 703 | 85.4 | 2.0 | 12.6 | 2.2 |
| 38 | 37.79 | 24 | 907 | 81.6 | 6.3 | 12.0 | 6.6 |
| 67 | 15.91 | 66 | 1 050 | 41.8 | 56.1 | 5.1 | 63.6 |
| 62 | 21.24 | 66 | 1 402 | 46.8 | 50.9 | 1.3 | 90.6 |
| 47 | 30.96 | 48 | 1 450 | 29.8 | 65.8 | 1.0 | 92.1 |
| 64 | 28.77 | 66 | 1 899 | 29.6 | 68.9 | 3.6 | 74.8 |
| 54 | 30.02 | 66 | 1 981 | 20.3 | 78.7 | 2.7 | 81.2 |
| 41 | 51.25 | 48 | 2 460 | 14.6 | 83.2 | 0.7 | 94.9 |
| 170 | 37.44 | 66 | 2 471 | 32.9 | 67.1 | 4.6 | 70.5 |
| 64 | 42.98 | 66 | 2 837 | 14.1 | 85.2 | 1.8 | 87.5 |
| 170 | 45.06 | 66 | 2 974 | 11.2 | 88.8 | 1.6 | 89.9 |
| 64 | 48.02 | 66 | 3 169 | 0 | 100 | 0 | 100 |
| 170 | 52.53 | 66 | 3 467 | 32.3 | 67.7 | 3.3 | 79.0 |

4. Biological Efficacy of DMDS on *Sclerotium rolfsii*

The results obtained are assembled in the following Table 7. For this fungus, a slight deterioration in the quality of the inoculum was observed over time. Nevertheless, the viability and the vitality are greatly affected from CT values of 900 to 1 000 g·h/m³ and total efficacy is obtained between 2 000 and 2 500 g·h/m³.

TABLE 7

Summary of all the readings expressed in terms of viability and vitality on *Sclerotium rolfsii* (X = number of grains)

| | | | | Viability | | Vitality | |
| | | | | | | Nm (Over | |
| X | C | T | CT | V | RV | 19 days) | RNm |
|---|---|---|---|---|---|---|---|
| 44 | 17.46 | 24 | 419 | 59.1 | 33.7 | 5.1 | 40.9 |
| 41 | 26.04 | 24 | 625 | 53.7 | 39.8 | 4.8 | 44.3 |
| 37 | 29.29 | 24 | 703 | 51.4 | 42.4 | 4.4 | 48.7 |
| 37 | 37.79 | 24 | 907 | 16.2 | 81.8 | 1.4 | 84.2 |
| 58 | 15.91 | 66 | 1 050 | 27.6 | 68.0 | 2.1 | 71.1 |
| 60 | 21.24 | 66 | 1 402 | 18.3 | 78.7 | 1.3 | 81.8 |
| 40 | 30.96 | 48 | 1 450 | 15.0 | 83.2 | 0.7 | 91.8 |
| 65 | 28.77 | 66 | 1 899 | 3.1 | 96.4 | 0.2 | 96.8 |
| 70 | 30.02 | 66 | 1 981 | 4.3 | 95.0 | 0.3 | 95.1 |
| 40 | 51.25 | 48 | 2 460 | 10.0 | 88.8 | 0.4 | 94.7 |
| 170 | 37.44 | 66 | 2 471 | 0 | 100 | 0 | 100 |
| 90 | 42.98 | 66 | 2 837 | 0 | 100 | 0 | 100 |
| 170 | 45.06 | 66 | 2 974 | 0 | 100 | 0 | 100 |
| 80 | 48.02 | 66 | 3 169 | 0 | 100 | 0 | 100 |
| 170 | 52.53 | 66 | 3 467 | 0 | 100 | 0 | 100 |

In summary, for the four species of fungi studied, DMDS causes a marked decrease in the population from CT doses of between 2 000 and 2 500 g·h/m³, or even at around 1 000 g·h/m³ in the case of *Sclerotinia* and *Sclerotium*, and total mortality for CT doses of between 3 000 and 3 500 g·h/m³, or even between 2 000 and 2 500 g·h/m³ for *Sclerotium*.

EXAMPLE 5

Nematicidal Properties

The nematicidal effect of dimethyl disulphide (DMDS), dipropyl disulphide (DPDS) and diallyl thiosulphinate (allicin), three major degradation products of allium, was demonstrated by in vitro tests carried out on larvae of *Meloidogyne arenaria*, a species among the root gall nematodes, which are highly noxious and extremely polyphagous and among the most widespread worldwide, on most vegetable crops, in particular those of tomato and strawberry plants which are the crops which consume the most methyl bromide.

Materials and Methods

The second-stage juvenile larvae (the free and infesting stage) are immersed for 24 hours in the test solution and then the number of larvae paralysed are counted before transferring them into pure water for another 24 hours. At the end of the 48 hours which have thus elapsed, the larvae paralysed are again counted and the larvae truly dead are counted the next day.

The breeding of the nematodes was carried out on tomato plants. The tests were carried out with, aqueous solutions of DMDS at 0.0001%, 0.1%, 1% and 5% by mass, of DPDS at 1%, 5% and 10% by mass, and of allicin at 0.0003%, 0.0015% and 0.003% by mass, compared with a control consisting of pure water, and repeated five times. The ovicidal activity was also evaluated according to the same modalities, by counting the number of hatchings after 5 to 20 days following exposure to the products.

Results

At a concentration of less than 1%, DMDS has only a very weak nematostatic activity and no nematicidal activity.

At a concentration of greater than or equal to 1%, DMDS and DPDS exhibit a high nematostatic and nematicidal activity, as clearly shown in Tables 8 and 9. Total efficacy (100% mortality) is obtained for concentrations of greater than or equal to 1% in the case of DPDS.

Allicin also exhibits a high nematostatic and nematicidal activity at much lower concentrations as shown in Table 10. However, total efficacy (100% mortality) was not evaluated in this case.

TABLE 8

Efficacy of dimethyl disulphide (DMDS) on the larvae

| Concentration by mass (%) | Immobility rate after 24 h (%) | Immobility rate after 48 h (%) | Mortality rate after 72 h (%) |
| --- | --- | --- | --- |
| 0 (control) | 8 | 6 | 9 |
| 1 | 72 | 84 | 80 |
| 5 | 97 | 98 | 98 |

TABLE 9

Efficacy of dipropyl disulphide (DPDS) on the larvae

| Concentration by mass (%) | Immobility rate after 24 h (%) | Immobility rate after 48 h (%) | Mortality rate after 72 h (%) |
| --- | --- | --- | --- |
| 0 (control) | 8 | 7 | 9 |
| 1 | 89 | 100 | 100 |
| 5 | 93 | 100 | 100 |
| 10 | 95 | 100 | 100 |

TABLE 10

Efficacy of allicin on the larvae

| Concentration by mass (%) | Immobility rate after 24 h (%) | Immobility rate after 48 h (%) | Mortality rate after 72 h (%) |
| --- | --- | --- | --- |
| 0 (control) | 2 | 10 | 8 |
| 0.0003 | 7 | 49 | 12 |
| 0.0015 | 19 | 85 | 45 |
| 0.003 | 49 | 65 | 63 |

As is evident from Tables 11 and 12, DMDS and DPDS also show a very high ovicidal activity. In both cases, an approximately 97% reduction is observed in the number of hatchings on the last day of observation.

TABLE 11

Efficacy of DMDS on the eggs of nematodes

| Concentration by mass (%) | Number of hatchings (cumulative) | | | |
| --- | --- | --- | --- | --- |
| | D5 | D10 | D13 | D17 |
| 0 (control) | 141 | 179 | 184 | 184 |
| 1 | 7 | 7 | 7 | 7 |
| 5 | 2 | 2 | 5 | 5 |
| 10 | 0 | 2 | 5 | 5 |

TABLE 12

Efficacy of DPDS on the eggs of nematodes

| Concentration by mass (%) | Number of hatchings (cumulative) | | | | |
| --- | --- | --- | --- | --- | --- |
| | D5 | D8 | D12 | D15 | D19 |
| (0) control | 550 | 810 | 990 | 1 030 | 1 030 |
| 1 | 117 | 183 | 200 | 200 | 200 |
| 5 | 67 | 67 | 67 | 67 | 67 |
| 10 | 33 | 33 | 33 | 33 | 33 |

EXAMPLE 6

Insecticidal Properties

The insecticidal activity of dimethyl disulphide (DMDS), of diallyldisulphide (DADS) and of diallyl thiosulphinate (allicin) was demonstrated by in vitro tests on a soil insect, a termite (*Reticulitermes santonensis*).

Materials and Methods:

Dead wood infested with termites was collected from the soil on ground occupied by a colony. This dead wood serves as breeding medium. The breeding is maintained at a constant 25° C. and a day/night 12:12 alternation.

The insects are removed in an amount of 2 soldiers per 28 workers.

The tests are carried out in hermetically closed glass jars having a volume of 3 L and containing the insects.

The product to be tested is introduced through a hole 2 mm in diameter with the aid of a micropipette and deposited on a filter paper (2×5 cm: Whatman No. 1) suspended at the centre of the jar where it migrates by capillarity and vaporizes rapidly. The hole is hermetically closed again as quickly as possible.

The jars are placed for 24 hours in an incubator under the same breeding conditions.

At the end of 24 hours, after a few instants of aeration, a first count is made and then the insects are placed again under breeding conditions for another 24 hours. The counting of the mortality is therefore carried out at the end of 48 hours. It is this final count which will serve to calculate the LC50 at 24 hours of fumigation, the first being only an indication of the variation post-treatment. Indeed, numerous fumigants have a "knock down" effect which can suggest death for insects which prove to be alive on the next day after recovering. Each test is carried out on a population of 30 to 50 insects and is accompanied by a control without treatment. Several repeats are carried out with doses close to the LC50.

TABLE 13

| Results (Probits method) | | | |
|---|---|---|---|
|  | DMDS | DADS | Allicin |
| LC50 in g × 24 h/m³ | 0.095 | 0.011 | 0.010 |

CONCLUSION

As indicated in Table 13, the 3 products tested show an excellent insecticidal activity on the insect in the soil used. The activity of DADS, which is close to that of allicin, is greater than that of DMDS, which is itself comparable to that of methyl bromide (0.1 g×24 h/m³).

EXAMPLE 7

Effects on Microorganisms

The effect of DMDS, applied at 150 kg/ha in the form of formulation A, to soil microorganisms was evaluated according to the following standard methods:

"Recommended tests for assessing the side-effects of pesticides on the soil micro flora", Technical Report Agricultural Research Council Weed Research Organization, 1980 (59).

"OECD Guideline for Testing of Chemicals—Soil Microorganisms: Carbon Mineralization Test", Draft document, June 1996.

The effect of DMDS on soil microorganisms is measured by the reduction in the oxygen consumed by these microorganisms, expressed in mg $O_2$ per kg of dry soil per h, 14, 28, 42, 57 days after the treatment (Table 14).

TABLE 14

|  | Day 0 | Day 14 | Day 28 | Day 42 | Day 57 |
|---|---|---|---|---|---|
| Untreated control | 11.23 | 10.18 | 7.87 | 9.12 | 7.30 |
| DMDS 150 kg/ha | 9.70 | 8.74 | 6.62 | 8.93 | 4.90 |

Table 14 shows a significant reduction in the oxygen consumed by the microorganisms, attributed to reduction in their population.

The invention claimed is:

1. A pesticidal treatment of soils or plant substrates, comprising treating said soils or plant substrates by fumigation, with dimethyl disulfide at a dose of between 150 and 1000 kg/ha in the soil or in the substrate, whereby a combined nematocidal, fungicidal, insecticidal and bactericidal effect is achieved.

2. The treatment according to claim 1, in which dimethyl disulfide is applied in the pure state or in the form of an aqueous emulsion, a microemulsion, a solution in water or a solution in an organic solvent.

3. The treatment according to claim 1, in which the dimethyl disulfide has no phytotoxic effect.

4. The treatment according to claim 1, combined with a simultaneous or non-simultaneous treatment with one or more other pesticidal substances.

* * * * *

UNITED STATES PATENT AND TRADEMARK OFFICE
CERTIFICATE OF CORRECTION

| | | |
|---|---|---|
| PATENT NO. | : 8,663,669 B2 | Page 1 of 1 |
| APPLICATION NO. | : 13/164584 | |
| DATED | : March 4, 2014 | |
| INVENTOR(S) | : Thierry Aubert et al. | |

It is certified that error appears in the above-identified patent and that said Letters Patent is hereby corrected as shown below:

On the Title Page
Item (30) insert -- Foreign Application Priority Data
March 19, 2001  (FR)  01/03674 --

Signed and Sealed this
First Day of July, 2014

Michelle K. Lee
*Deputy Director of the United States Patent and Trademark Office*